United States Patent [19]
Follese et al.

[11] Patent Number: 5,495,988
[45] Date of Patent: Mar. 5, 1996

[54] HYPODERMIC NEEDLE GRINDER

[76] Inventors: Robert D. Follese, 3951 NW. 4th Ct., Coconut Creek, Fla. 33066; Felix Castro, 577 NW. 87th Terr., Coral Springs, Fla. 33071

[21] Appl. No.: 273,458

[22] Filed: Jul. 11, 1994

[51] Int. Cl.⁶ .............................. B02C 23/00; B24B 7/08
[52] U.S. Cl. .............................. 241/36; 241/99; 241/100; 241/606; 451/282; 451/382
[58] Field of Search .......................... 241/36, 99, 278.1, 241/100, 60, 606; 451/278, 282, 331, 382, 549

[56] References Cited

U.S. PATENT DOCUMENTS

| | | | |
|---|---|---|---|
| 3,322,355 | 5/1967 | Bryant | 241/186 |
| 3,750,966 | 8/1973 | Anderson | 241/606 X |
| 3,926,379 | 12/1975 | Dryden et al. | 241/69 |
| 3,929,295 | 12/1975 | Montalbano | 241/190 |
| 4,205,794 | 6/1980 | Horton et al. | 241/73 |
| 4,531,437 | 7/1985 | Szablak et al. | 241/100 X |
| 4,809,915 | 3/1989 | Koffsky et al. | 241/36 |
| 4,971,261 | 11/1990 | Solomons | 241/606 X |
| 5,025,994 | 6/1991 | Maitlen et al. | 241/99 |
| 5,064,124 | 11/1991 | Chang | 241/33 |
| 5,167,374 | 12/1992 | Strohmeyer | 241/36 |
| 5,186,402 | 2/1993 | Lin | 451/282 X |
| 5,282,428 | 2/1994 | Greville et al. | 241/606 X |
| 5,355,788 | 10/1994 | Phinney | 241/36 X |

FOREIGN PATENT DOCUMENTS

| | | | |
|---|---|---|---|
| 4103562 | 8/1991 | Germany | 241/606 |
| 92014096 | 8/1992 | WIPO | 241/606 |

*Primary Examiner*—Timothy V. Eley
*Attorney, Agent, or Firm*—Oltman and Flynn

[57] ABSTRACT

An apparatus for preparing hypodermic needle having a needle shaft with a pointed end and a hub end and having a needle hub joined to the hub end for safe disposal of the hypodermic needle includes a metal grinder assembly including a grinding member having a grinding surface and a mechanism for moving the grinding member, and a needle guide structure for holding the needle shaft adjacent to the grinding member and the pointed end oriented substantially toward the grinding surface, for guiding the needle shaft toward and against the grinding surface to progressively grind the needle shaft into very fine particles. The mechanism for moving the grinding member preferably includes an electric motor. The apparatus preferably additionally includes a housing enclosing the grinding member, having a housing wall. The needle guide structure preferably includes a needle opening in the housing wall adjacent to the grinding member into which the needle shaft is inserted to make contact with the grinding member, the needle opening retaining the needle against substantial lateral movement resulting from friction with the grinding member.

16 Claims, 2 Drawing Sheets

HYPODERMIC NEEDLE GRINDER

BACKGROUND OF THE INVENTION

1. Field of the Invention

The present invention relates generally to the field of medical waste disposal devices. More specifically, it relates to an apparatus for destroying hypodermic needles so that they cannot be inappropriately reused and cannot transmit disease by pricking a waste handler. The apparatus includes a grinder and a needle guide structure for directing the needle into the grinder. The grinder includes an electric motor having a motor drive shaft and a grinding wheel mounted on the drive shaft. The grinder is enclosed within a cylindrical housing having a first chamber containing the motor and a second chamber containing the wheel, the chambers being separated from each other by a partition member. The drive shaft extends through a port in the partition member. The second chamber includes an access wall opposite the partition wall, and a needle receptacle structure in the access wall in the form of an outer recess fitted with a photocell detection assembly. This detection assembly senses the insertion of a needle into the outer recess and activates the motor to rotate the grinding wheel. An inner recess receives and braces the needle hub and guides the needle shaft against the grinding wheel as the wheel grinds the needle shaft into fine grain particles. The particles fall into and collect in a tray in the lower end of the second chamber. The tray contains a replaceable liner sack and is removable for removal of a full liner sack and the particles contained therein and for replacement of the liner sack.

2. Description of the Prior Art

There have long been disintegration devices for battering and breaking medical waste items such as syringes. These devices almost invariably include a hopper for receiving the waste items, a disintegration chamber and a chute for delivering these items into the chamber. The disintegration chamber typically contains rotationally mounted and motor driven arrays of battering hammers or chains which spin and beat the waste items into bent pieces.

An example of such a device is that of Bryant, U.S. Pat. No. 3,322,355, issued on May 30, 1967. Bryant includes a tall housing with the waste hopper at the top, an angled waste carrying chute below the hopper for gradually delivering the waste into the disintegration chamber, a motorized axle extending through the chamber with a series of radially mounted hammer members extending therefrom, and a collection bin in the bottom of the housing. Dryden, et al., U.S. Pat. No. 3,926,379, issued on Dec. 16, 1975, teaches a hypodermic syringe disintegrator. Dryden is very similar to Bryant except that the hopper is largely eliminated and an oscillating pump circulates disinfectant liquid through the waste material path. The collection bin includes a disposable waste bag, from which accumulated disinfectant liquid is pumped back up into the inlet waste chute. Horton, et al., U.S. Pat. No. 4,205,794, issued on Jun. 3, 1980, reveals a hypodermic syringe destruction device. Horton is much like Dryden except that the hammer elements are replaced with functionally similar flexible chain members. The chain members swing radially on a shaft within the destruction chamber, and flex upon striking large objects to be comminuted. An arcuate screen is positioned adjacent the chain member distal ends to permit passage of comminuted articles. Koffasky et al., U.S. Pat. No. 4,809,915, issued on Mar. 7, 1989, teaches a waste disposal apparatus much like those mentioned above, except that the hammer members in the destruction chamber have sharpened edges to act as cutting blades. Chopped waste items are collected in a lined container below the chamber, and the container rides on a cart. Montalbono, U.S. Pat. No. 3,929,295, issued on Dec. 30, 1975, teaches an apparatus for destroying syringes and like articles. The waste articles are advanced between serrated stationary elements and serrated moving elements to bend and cut the waste articles. Maitlen, et al., U.S. Pat. No. 5,025,994, issued on June 25, 1991, discloses an apparatus for cutting up hypodermic syringes or needles. Maitlen includes a plurality of cylindrical rotors within a chamber, each rotor having radially extending teeth which interact with each other to cut the syringes and needles. The word "grinding" is used in Maitlen, but the action performed is more that of cutting and breaking. Chang, U.S. Pat. No. 5,064,124, issued on Nov. 12, 1991, teaches a medical waste disposal system. Chang mentions some sort of grinding assembly, but does not explain its structure.

Problems with these devices include their substantial bulk and expense. A more important problem is that, while a syringe needle may be bent or broken in one or two places, it still retains its ability to prick and penetrate the skin, and thereby to transmit deadly diseases to waste handlers. FIG. 1B of Montalbono shows the results of such waste processing, and the needle is shown to be simply bent, and still dangerous. And where waste is improperly or illegally dumped, the sharp needles may be spread around a neighborhood or a beach where children may step on them. These expensive, prior devices fail to effectively disarm what may be the most deadly element of medical waste.

It is thus an object of the present invention to provide a grinding apparatus which can receive all sizes and lengths of used hypodermic needles and quickly grind the needle shaft into a mass of very fine particles for safe disposal with no risk of accidental skin penetration or improper reuse to minimize the spread of contagious diseases.

It is another object of the present invention to provide such an apparatus which both conceals and holds the needle shaft steady during the grinding operation for ease and safety of handling.

It is still another object of the present invention to provide such an apparatus which is self-activating, so that when a needle is inserted into the apparatus, the grinding elements within the apparatus automatically activate, and then deactivate upon removal of the remaining plastic needle hub.

It is finally an object of the present invention to provide such an apparatus which delivers the ground particles into a sealed container having a liner for ready disposal, and to provide such an apparatus which is simple, compact, portable, reliable and inexpensive to manufacture.

SUMMARY OF THE INVENTION

The present invention accomplishes the above-stated objectives, as well as others, as may be determined by a fair reading and interpretation of the entire specification.

An apparatus is provided for preparing a hypodermic needle having a needle shaft with a pointed end and a hub end and having a needle hub joined to the hub end for safe disposal of the hypodermic needle, including a metal grinder assembly including a grinding member having a grinding surface and a mechanism for moving the grinding member, and a needle guide structure for holding the needle shaft adjacent to the grinding member and the pointed end oriented substantially toward the grinding surface, for guiding the needle shaft toward and against the grinding surface to progressively grind the needle shaft into very fine particles. The mechanism for moving the grinding member preferably includes an electric motor. The apparatus preferably additionally includes a housing enclosing the grinding member, having a housing wall. The needle guide structure preferably includes a needle opening in the housing wall adjacent to the grinding member into which the needle shaft is inserted to make contact with the grinding member, the needle opening retaining the needle against substantial lateral movement resulting from friction with the grinding member. A cable is preferably provided for delivering electric current to the motor from a power source for powering the motor, the cable having a switch, where the needle guide structure includes a recess in the housing wall, the recess having a recess bottom wall in which the needle opening is located, and having a side wall in which a needle detecting assembly is mounted for detecting the presence of a needle in the recess and for simultaneously activating the switch to activate the motor. The needle detection assembly preferably includes a light source for generating a beam of light across the recess for interruption by the insertion of the needle into the needle hole, and a photocell sensor assembly for sensing an interruption of the beam of light. The needle detection assembly alternatively includes an electric eye assembly or a reed lever assembly. The housing preferably includes a lower portion including a particle collection tray in which the particles are collected for periodic removal. The tray preferably contains a removable liner for retaining the particles during removal of the particles from the tray. The tray is optionally removably joined to the housing with a tray connection structure. The housing wall may extend to substantially enclose the motor. The particle disposal container, has a vacuum assembly for evacuating the particles into the disposal container. The power source may include a battery or a wall outlet or a junction box.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figure 1:
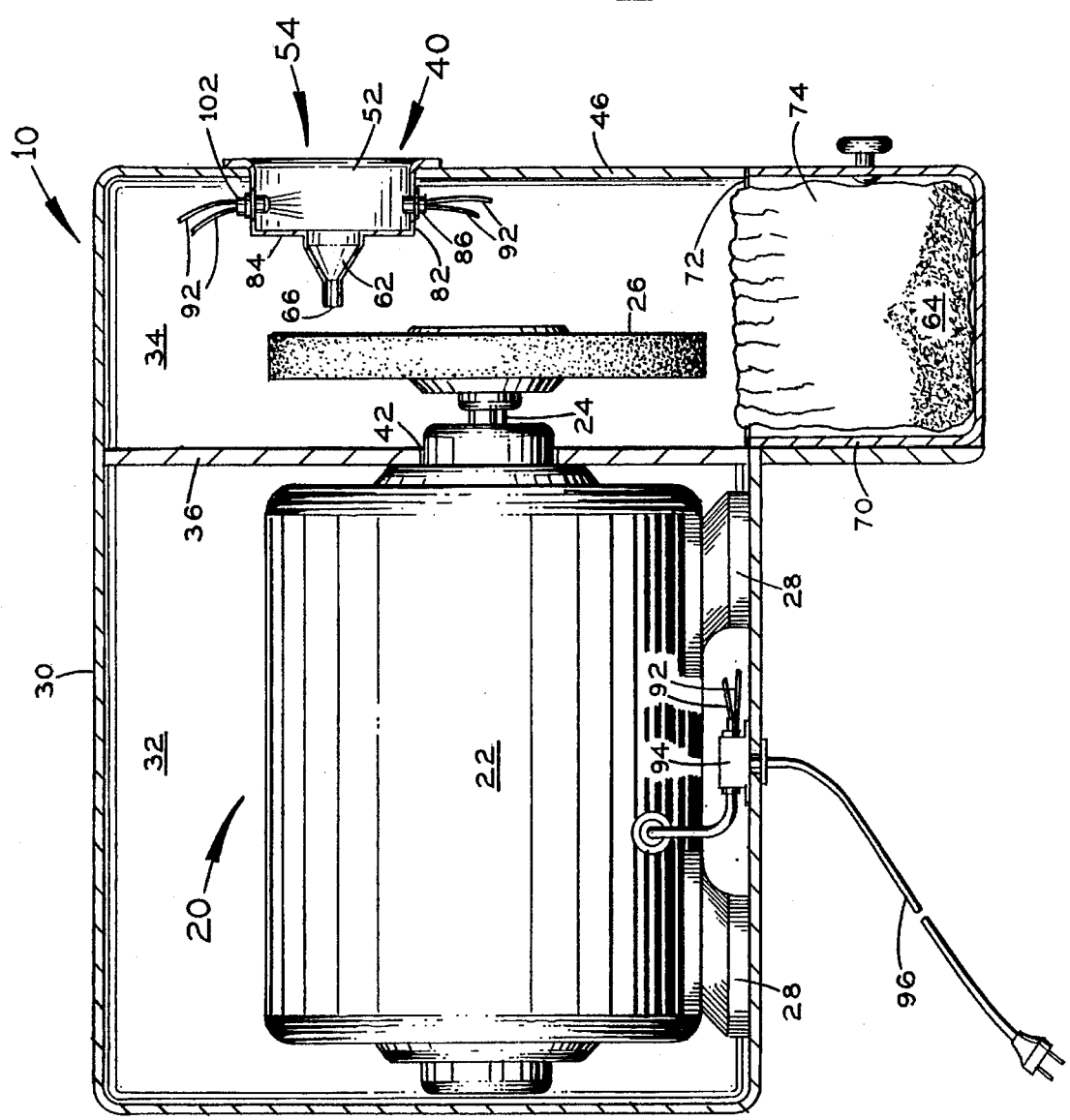
FIG. 1 is a cross-sectional side view of the inventive apparatus revealing the first and second chambers of the housing and the grinder motor and wheel, and the construction of the needle guide structure.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Figure 3:
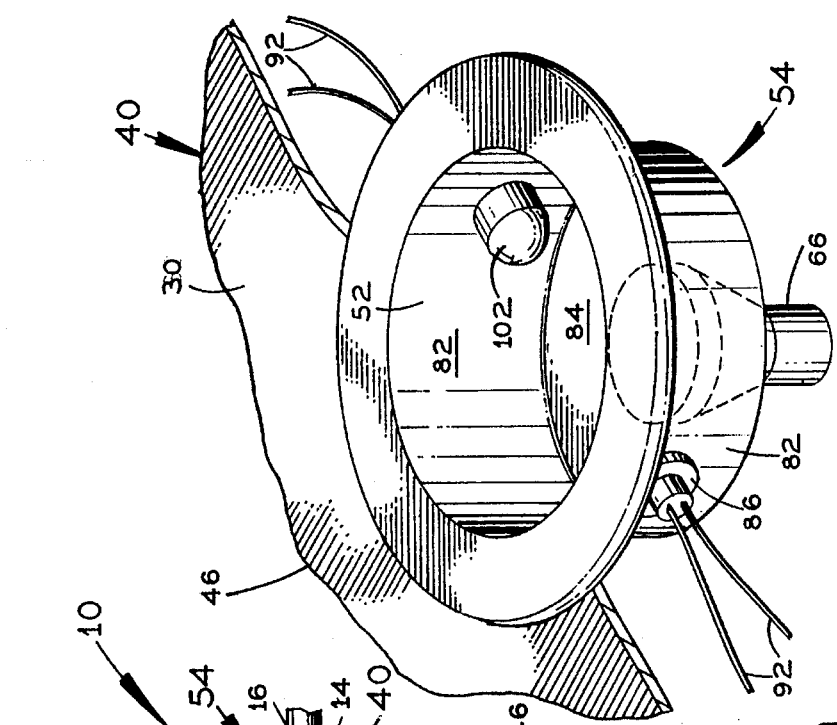
FIG. 3 is a perspective view of the needle guide structure alone.
Figure 2:
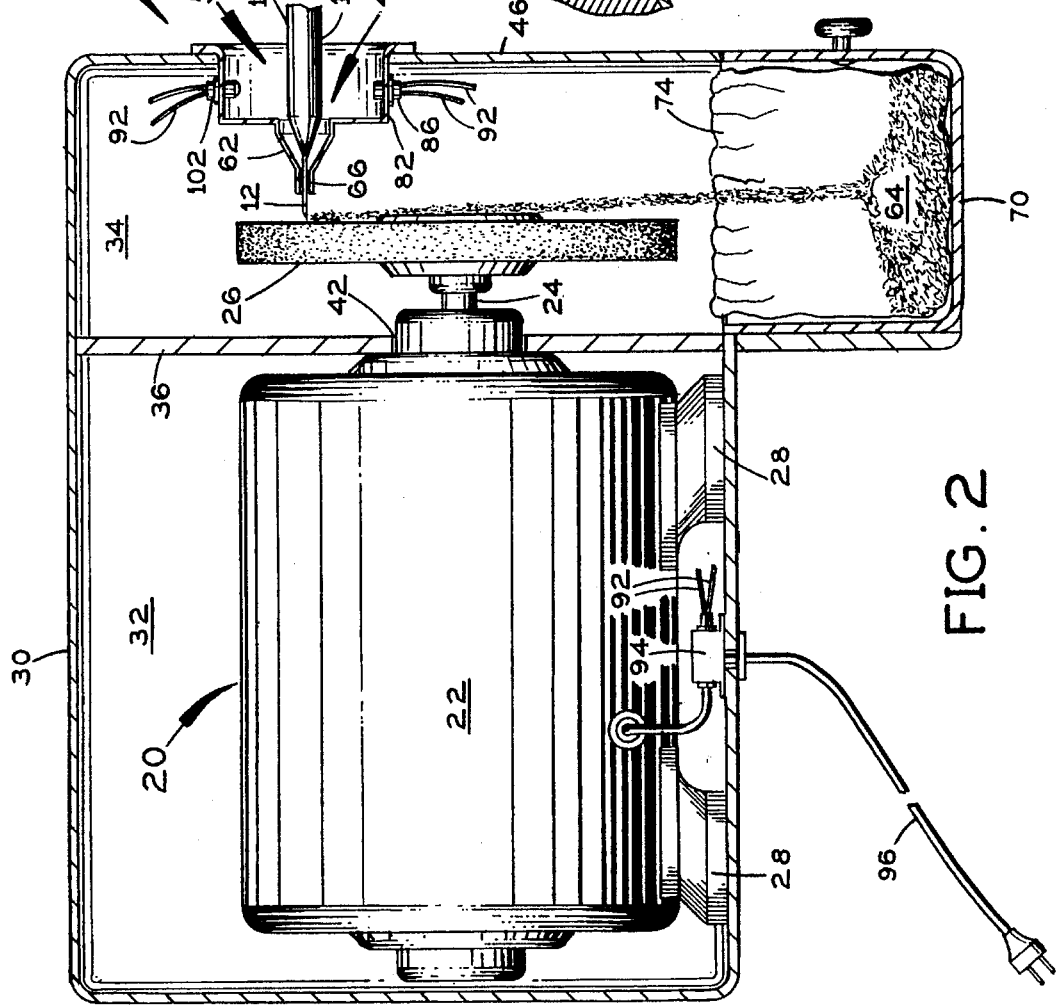
FIG. 2 is a view as in FIG. 1, but with a needle being inserted into the needle guide structure for grinding and disposal.

Referring to FIGS. 1–3, an apparatus 10 is disclosed for safely destroying the pointed tubular shafts 12 extending from the hub 14 of used hypodermic needles 16. Apparatus 10 preferably includes a conventional grinder assembly 20 in the form of an electric motor 22 having a motor drive shaft 24 and a grinding wheel 26 mounted on drive shaft 24. Grinder assembly 20 is contained within a cylindrical housing 30 which includes a guide structure 40 for directing the shaft 12 against wheel 26.

Housing 30 includes a first chamber 32 and a second chamber 34 separated from each other by a partition member 36. Motor 22 is mounted on mounts 28 within first chamber 32. Drive shaft 24 extends through a port 42 in partition member 36 into second chamber 34 to grinding wheel 26 which is contained within second chamber 34. Second chamber 34 includes an access wall 46 opposite partition wall 36. Needle guide structure 40 is formed in access wall 46 and includes an outer recess 52 fitted with a photocell detection assembly 54. Assembly 54 senses the insertion as well as the removal of a needle hub 14 into outer recess 52 and activates and deactivates motor 22, respectively, to rotate grinding wheel 26 only when a needle shaft 12 is in position. An inner recess 62 is provided within outer recess 52. Inner recess 62 is sized to snugly receive and brace needle hub 14 and includes a needle port 66 for receiving and guiding a needle shaft 12 against grinding wheel 26, as wheel 26 progressively grinds needle shaft 12 into fine grain particles 64. Particles 64 fall from wheel 26 into and collect in a removable tray 70 in the bottom end 72 of second chamber 34. Tray 70 contains a replaceable liner sack 74 and is removable for removal of a full liner sack 74 and particles 64 and for replacement of liner sack 74 in tray 70.

Outer recess 52 has a cylindrical side wall 82 and a circular bottom wall 84. Photocell detection assembly 54 preferably includes a photocell 86 wired with conventional circuitry 92 to a switch 94 in the motor 22 power cable 96. A light source 102 is provided in side wall 82 opposite and directed toward photocell 86 to deliver a continuous beam of light to photocell cell 86 until broken by the interposition of a needle hub 14. See FIGS. 2 and 3. Motor 22 preferably operates on standard household or hospital voltages and currents, but may also operate on 12, 24, 120 or 240 volts.

Apparatus 10 is compact and portable, and fixedly mountable to a wide variety of surfaces, such as to a desk or wall. Apparatus 10 may be oriented such that needle port 66 and grinding wheel 26 are positioned to receive a needle shaft 12 fed vertically, horizontally, or from any position therebetween.

The power source may be a wall outlet, a battery or a junction box, or any other suitable source. Liner sacks 74 may be formed of paper, fiber, plastic, mesh nylon, or of any other suitable material. Photocell detection means 54 may be equivalently replaced with a conventional electric eye assembly or reed lever assembly (not shown). Grinding wheel 26 is preferably formed of an abrasive carbide material. A vacuum assembly (not shown) may evacuate particles 64 from tray 70.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A compact and portable apparatus for preparing a hypodermic needle having a needle shaft with a pointed end and a hub end and having a needle hub joined to said hub end for safe disposal of said hypodermic needle, the compact and portable apparatus comprising:

metal grinder means comprising a grinding member having a grinding surface and means for moving said grinding member, needle guide means for holding said needle shaft adjacent to said grinding member and said pointed end oriented substantially toward said grinding surface, for guiding said needle shaft toward and against said grinding surface to progressively grind said shaft into particles, a cable for delivering electric current to said motor from a power source for powering said motor, said cable having electrical switch means, and wherein said need guide means comprises a recess in said housing wall, said recess having a recess bottom wall in which said needle opening is located, and having a side wall in which an optical needle detecting means are mounted for detecting the presence of a needle in said recess and for simultaneously activating said electrical switch means to activate said motor.

2. The compact and portable apparatus of claim 1, wherein said means for moving said grinding member comprises an electric motor.

3. The compact and portable apparatus of claim 1, additionally comprising a housing enclosing said grinding member, having a housing wall.

4. The compact and portable apparatus of claim 3, wherein said needle guide means comprises a needle opening in said housing wall adjacent said grinding member into which said needle shaft is inserted to make contact with said grinding member, said needle opening retaining said needle against substantial lateral movement resulting from friction with said grinding member.

5. The compact and portable apparatus of claim 3, wherein said housing comprises a lower portion and wherein said lower portion comprises a particle collection tray in which said particles are collected for periodic removal.

6. The compact and portable apparatus of claim 5, wherein said tray contains a removable liner sack for retaining said particles during removal of said particles from said tray.

7. The compact and portable apparatus of claim 5, wherein said tray is removably joined to said housing with tray connection means.

8. The compact and portable apparatus of claim 3, wherein said housing wall extends to substantially enclose said motor.

9. The compact and portable apparatus of claim 1, wherein said needle detection means comprises:

a light source for generating a beam of light across said recess for interruption by the insertion of a said needle into said needle hole, photocell sensor means for sensing an interruption of said beam of light.

10. The compact and portable apparatus of claim 1, wherein said needle detection means comprises an electric eye assembly.

11. The compact and portable apparatus of claim 1, additionally comprising:

a particle disposal container, vacuum means for evacuating said particles into said disposal container.

12. The compact and portable apparatus of claim 1, wherein said power source comprises a battery.

13. A compact and portable apparatus for preparing a hypodermic needle having a needle shaft with a pointed end and a hub end and having a needle hub joined to said hub end for safe disposal of said hypodermic needle, the compact and portable apparatus comprising:

metal grinder means comprising a grinding member having a grinding surface and means for moving said grinding member, needle guide means for holding said needle shaft adjacent to said grinding member and said pointed end oriented substantially toward said grinding surface, for guiding said needle shaft toward and against said grinding surface to progressively grind said shaft into particles, a cable for delivering electric current to said motor from a power source for powering said motor, said cable having electrical switch means, and wherein said needle guide means comprises a recess in said housing wall, said recess having a recess bottom wall in which said needle opening is located, and having a side wall in which a needle detecting means having a reed lever assembly, are mounted for detecting the presence of a needle in said recess and for simultaneously activating said electrical switch means to activate said motor.

14. The compact and portable apparatus of claim 13, wherein said means for moving said grinding member comprises an electric motor.

15. The compact and portable apparatus of claim 13, wherein said apparatus comprises a lower portion and wherein said lower portion comprises a particle collection tray in which said particles are collected for periodic removal.

16. The compact and portable apparatus of claim 15, wherein said tray contains a removable liner sack for retaining said particles during removal of said particles from said tray.

* * * * *